US00PP28666P3

(12) United States Plant Patent
Finn

(10) Patent No.: US PP28,666 P3
(45) Date of Patent: Nov. 21, 2017

(54) RED RASPBERRY PLANT NAMED 'KOKANEE'

(50) Latin Name: ***Rubus idaeus* L.**
Varietal Denomination: KOKANEE

(71) Applicant: The United States of America, as represented by the Secretary of Agriculture, Washington, DC (US)

(72) Inventor: Chad E. Finn, Corvallis, OR (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/999,027

(22) Filed: Mar. 21, 2016

(65) Prior Publication Data

US 2017/0290220 P1 Oct. 5, 2017

(51) Int. Cl.
*A01H 5/08* (2006.01)

(52) U.S. Cl.
USPC ..... Plt./204

(58) Field of Classification Search
USPC ..... Plt./204
CPC ..... A01H 5/0887
See application file for complete search history.

*Primary Examiner* — Kent L Bell

(74) *Attorney, Agent, or Firm* — John D. Fado; Gail E. Poulos

(57) ABSTRACT

A new and distinct red raspberry cultivar distinguished by its moderate to high yields of large, bright-red-colored, firm, conic, sweet, flavorful fruit with excellent fresh fruit quality borne on primocanes in late summer

3 Drawing Sheets

Latin name of the genus and species of the plant claimed: 'KOKANEE' is a new red raspberry plant that is a *Rubus idaeus* L.

Variety denomination: The new red raspberry plant claimed is of the variety denominated 'KOKANEE' containing *Rubus idaeus* germplasm.

BACKGROUND OF THE INVENTION

The present invention relates to a new and distinct raspberry cultivar designated 'Kokanee' and botanically known as *Rubus idaeus* L.

This new raspberry cultivar was discovered in Corvallis, Oreg. in September 2009 and originated from cross of ORUS 1173-2 (unpatented) and 'Vintage' (U.S. Plant Pat. No. 24,198); (herein incorporated by reference in its entirety). The new cultivar is firmer and more uniformly shaped than its maternal parent, and later ripening and more conically shaped than the paternal parent. 'Kokanee's closest comparison cultivars are its paternal parent 'Vintage' (supra) and 'Heritage' (supra). 'Kokanee' is later ripening and more vigorous than 'Vintage' (supra) and earlier ripening and bears large and lighter colored fruit than 'Heritage' (supra). The new cultivar has been asexually reproduced annually since 2009 by the use of root cuttings in Corvallis Oreg. The new cultivar was established in vitro from a cane cutting and microcuttings have been rooted from this sort of culture. The new raspberry plant has been found to be stable and reproduce true to type through successive asexual propagations.

SUMMARY OF THE INVENTION

The following are the most outstanding and distinguishing characteristics of this new cultivar when grown under normal horticultural practices in Oreg.: 1. firmer and more uniformly shaped than the maternal parent ORUS 1173-2; 2. later ripening and more conically shaped than the paternal parent 'Vintage'; and 3. moderate to high yields of large, bright-red-colored, firm, conic, sweet, flavorful fruit with excellent fresh fruit quality borne on primocanes in late summer.

BRIEF DESCRIPTION OF THE PHOTOGRAPHS

The accompanying color photographs show typical specimens of the new cultivar at various stages of development as nearly true as it is possible to make in color reproductions.

Figure 1:
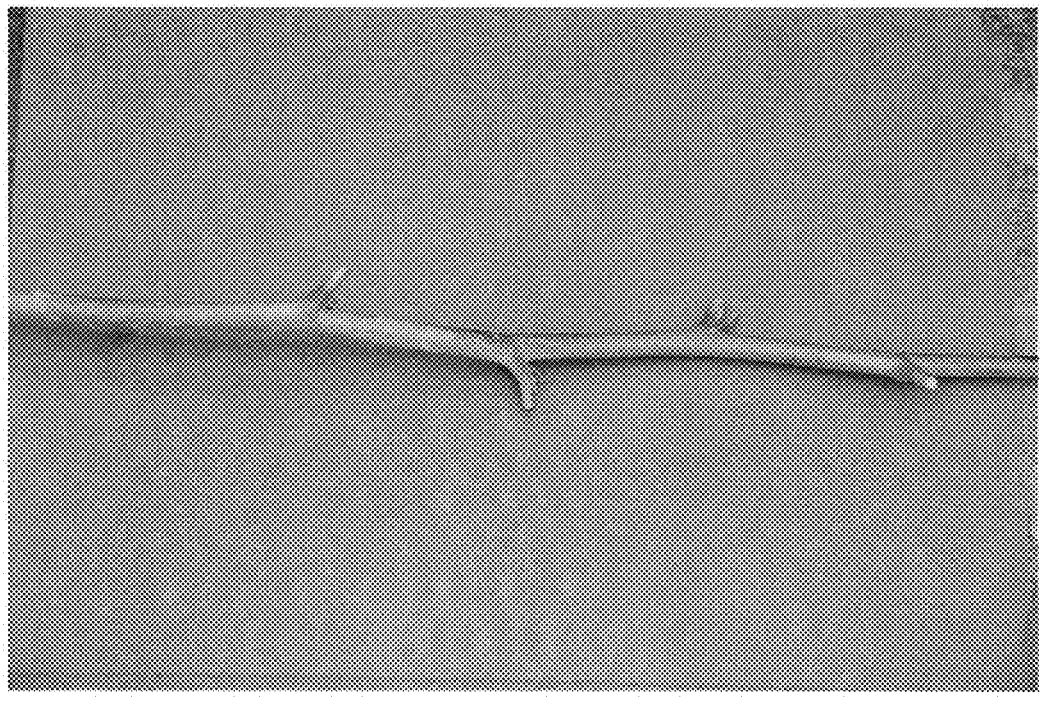

FIG. 1. Shows a section of young cane showing glaucosity and sparseness of prickles.

Figure 2:
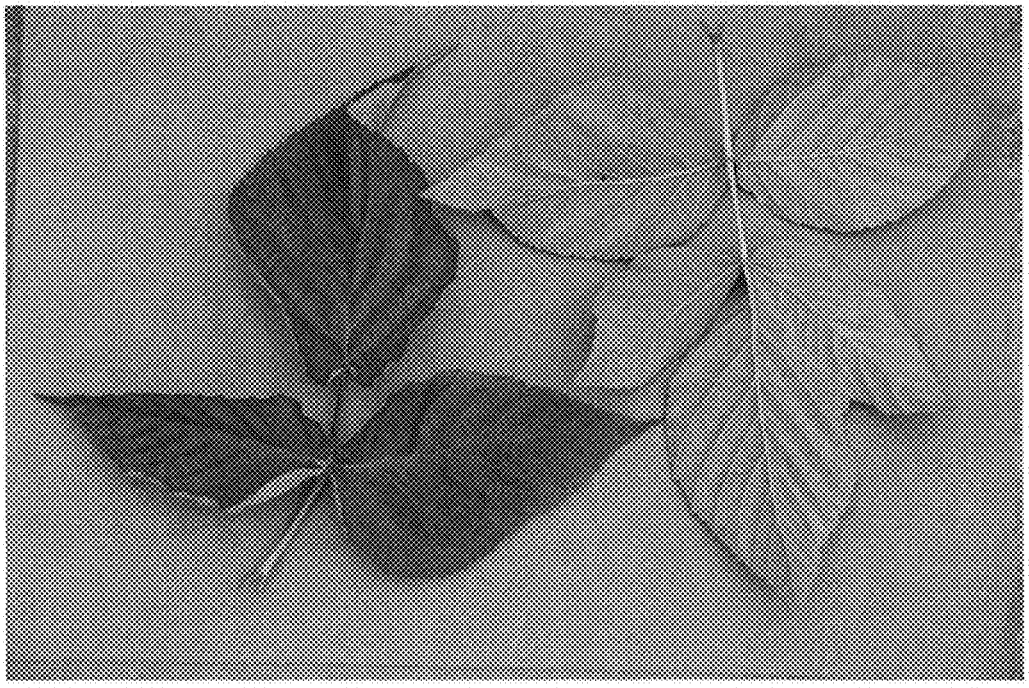

FIG. 2. Shows the upperside and underside of the plant leaves.

Figure 3:
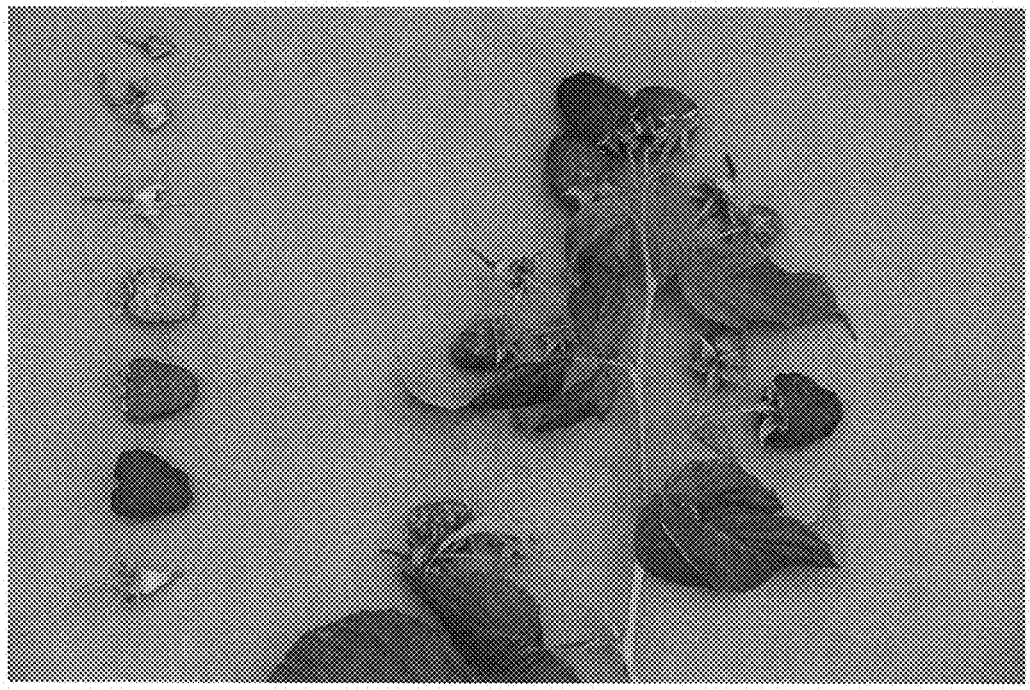

FIG. 3. Shows a range of developmental stages including unopened flower buds, mature open flowers, an immature fruit, a mature fruit without the receptacle, a receptacle with the fruit removed, and a fruiting lateral with ripe fruit.

The colors shown are as true as can be reasonably obtained by conventional photographic procedures.

DETAILED DESCRIPTION OF THE NEW CULTIVAR

The following is a detailed description of the botanical and pomological characteristics of the subject raspberry 'Kokanee' based on observations taken from 2010 to 2015 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'Kokanee' has not been observed under all possible environmental conditions. Color terminology follows The Royal Horticultural Society Colour chart. London (R.H.S.) ($5^{th}$ edition, 2007).

The descriptions reported herein are from 2-4 year-old specimens grown in Corvallis and Aurora, Oreg. with the measurements/observations for one trait always being made on samples from the same location. The plants used for these observations were planted in 2009-2012.

Table 1 shows plant characteristics of the new cultivar. Characteristics include plant size, plant diameter/density/vigor, and number of canes per hill.

TABLE 1

| Characteristic | 'Kokanee' |
|---|---|
| Plant size | Large |
| Plant height (cm) | 119.2 |
| Plant diameter/density/vigor | Medium to dense, tall, slender |
| Number of canes per hill | 100.1 |

Table 2 shows primocane characteristics of the new cultivar. Cane characteristics include new cane habit, timing of young shoots emergence from soil, number of young shoots, very young shoots intensity of anthocyanin coloration, diameter at 1.2 m from base, cane cross-section, length at time of fruit formation, number of nodes, internode length—node 2 to 3 from base, internode length—midpoint, internode length—node 5 to 6 from terminus, cane color, pubescence on canes, percent of cane length flowering as primocane, primocane strength: full-grown after picking, and glaucosity of primocane full-grown after picking.

TABLE 2

| Characteristic | 'Kokanee' |
|---|---|
| New cane habit | Erect |
| Timing of young shoots emergence from soil | Mid-April |
| Number of young shoots | 51.3 |
| Very young shoots intensity of anthocyanin coloration | Absent |
| Diameter at 1.2 m from base (cm) | 0.79 |
| Cane cross-section | Round |
| Length at time of fruit formation (m) | 1.94 |
| Number of nodes | 33.17 |
| Internode length—node 2 to 3 from base (cm) | 3.47 |
| Internode length—midpoint (cm) | 7.77 |
| Internode length—node 5 to 6 from terminus (cm) | 7.28 |
| Cane color | N144D yellow-green with occasional blush of 183D greyed-purple and occasional glaucosity of N155A white |
| Pubescence on canes | Absent |
| Percent of cane length flowering as primocane (%) | 36.20 |
| Primocane strength: full-grown after picking | Strong |
| Glaucosity of primocane full-grown after picking | Weak |

Table 3 shows prickle characteristics of the new cultivar. Prickle characteristics include presence of prickles on young shoots, prickle size, length of prickles (1 m from ground at end of growing season), and density of prickles—central ⅓ of cane, prickle texture, attitude of spine tips, and prickle color.

TABLE 3

| Characteristic | 'Kokanee' |
|---|---|
| Prickles on young shoots | Present |
| Prickle size | Medium |
| Length of prickles (1 m from ground at end of growing season) (cm) | 0.16 |

TABLE 3-continued

| Characteristic | 'Kokanee' |
|---|---|
| Number of prickles on 10 cm section of mature primocane taken at midpoint of cane (dense/medium/sparse/absent) | Medium, 352 |
| Prickle texture | Soft, stout |
| Attitude of spine tips | Horizontal |
| Prickle color | N144D yellow-green |

Table 4 shows primocane leaf characteristics of the new cultivar. Primocane leaf characteristics include primocane leaves: time of budbreak, petiole length (range), petiole length, petiole color—upper surface, petiole color—lower surface, petiole diameter, petiole color—upper surface, petiole color—lower surface, prickle distribution on petioles, rachis length, rachis color, stipule length, stipule orientation, leaf arrangement, number of leaves per node, entire leaf length, entire leaf width, number of leaflets per leaf, terminal leaflet length, terminal leaflet width, terminal leaflet shape, terminal leaflet tip/apex, terminal leaflet base, terminal leaflet cross section—plane, terminal leaflet shape of teeth, terminal leaflet margin, terminal leaflet petiolule length, terminal leaflet petiolule width, distal lateral leaflet length, distal lateral leaflet width, distal lateral leaflet petiolule length, basal lateral leaflet length, basal lateral leaflet width, basal lateral leaflet petiolule length, color of upper surface of leaflet, color lower surface of leaflet, and glossiness.

TABLE 4

| Characteristic | 'Kokanee' |
|---|---|
| Petiole length (cm) (range) | 2.92-3.86 |
| Petiole length (cm) | 3.37 |
| Petiole diameter (cm) | 0.19 |
| Petiole color—upper surface | 144C yellow-green with blush of 183D greyed-purple |
| Petiole color—lower surface | 144D yellow-green |
| Prickle distribution on petioles | Sparse |
| Rachis length (cm) | 1.42 |
| Rachis diameter (cm) | 0.17 |
| Rachis color | 144C yellow-green |
| Stipule length (cm) | 0.65 |
| Stipule width (cm) | 3.7 |
| Stipule orientation | Erect |
| Leaf arrangement | Compound, alternate |
| Number of leaves per node | One |
| Entire leaf length (cm) | 23.15 |
| Entire leaf width (cm) | 22.82 |
| Number of leaflets per leaf | Usually three; ranges from one to five |
| Terminal leaflet length (cm) | 13.17 |
| Terminal leaflet width (cm) | 7.73 |
| Terminal leaflet shape | Ovate |
| Terminal leaflet tip/apex | Broadly acuminate |
| Terminal leaflet base | Ovate |
| Terminal leaflet cross section-plane | Convex |
| Terminal leaflet shape of teeth | Acute |
| Terminal leaflet margin | Serrate |
| Terminal leaflet petiolule length (cm) | 1.64 |
| Terminal leaflet petiolule width (cm) | 0.19 |
| Distal lateral leaflet length (cm) | 9.82 |
| Distal lateral leaflet width (cm) | 4.77 |
| Distal lateral leaflet petiolule length | Sessile |
| Basal lateral leaflet length (cm) | 11.78 |
| Basal lateral leaflet width (cm) | 7.23 |
| Basal lateral leaflet petiolule length (cm) | Sessile |
| Color of upper surface of leaflet | 137A green |
| Color lower surface of leaflet | 191B greyed-green |
| Glossiness | Matte |

Table 5 shows flower characteristics of the new cultivar. Flower characteristics include timing of flower bud burst— primocane, bud shape—top view, bud shape—side view, bud length, bud diameter, bud color, flower diameter sepal—sepal, flower diameter petal—petal, diameter of calyx relative to corolla, flower depth (base to top of stigmas), number of nodes/lateral (all nodes are flowering nodes), number of nodes per lateral with >one flower, number of buds, flowers, fruit per lateral, number of buds, flowers, fruits per node of lateral, petal number, petal length, petal width, petal shape, petal apex, petal base, petal margin, color petals, sepal number, sepal length, sepal width, sepal shape, sepal apex, sepal margin, color sepals—inner surface, color sepals—outer surface, pedicel length, pedicel diameter, pedicel texture, color pedicels, stamen number, filament color, anther length, anther width, anther color—fresh, anther color—dry, pollen color, pistil number, stigma color, stigma shape, style length, style color, and ovary color, as well as measurements related to flowering laterals including peduncle length, peduncle diameter, peduncle texture, and peduncle color.

TABLE 5

| Characteristic | 'Kokanee' |
|---|---|
| Timing of flower bud burst—primocane | 1Aug. |
| Bud shape—top view | Pentagonal to rounded and undulate |
| Bud shape—side view | Deltoid |
| Bud length (cm) | 0.085 |
| Bud diameter (cm) | 0.068 |
| Bud color | 144B yellow-green |
| Flower diameter sepal-sepal (cm) | 2.00 |
| Flower diameter petal-petal (cm) | 1.35 |
| Diameter of calyx relative to corolla | 0.15 |
| Flower depth (base to top of stigmas) (cm) | 0.71 |
| Number of nodes/lateral (all nodes are flowering nodes) | 3.67 |
| Number of nodes per lateral with > one flower | 2.33 |
| Number of buds, flowers, fruit per lateral | 8.67 |
| Number of buds, flowers, fruits per node of lateral | 3.83 |
| Petal number | 5.83 |
| Petal length (mm) | 6.89 |
| Petal width (mm) | 3.64 |
| Petal shape | Oblanceolate |
| Petal apex | Rounded and undulate |
| Petal base | Cuneate |
| Petal margin | Entire |
| Color petals | NN155B |
| Sepal number | 5.83 |
| Sepal length (mm) | 9.31 |
| Sepal width (mm) | 4.69 |
| Sepal shape | Ovoid |
| Sepal apex | Cuspidate |
| Sepal margin | Entire |
| Color sepals—inner surface | 145B yellow-green |
| Color sepals—outer surface | 144B yellow-green at base fading to 144D yellow-green at edges |
| Pedicel length (mm) | 23.29 |
| Pedicel diameter (mm) | 0.93 |
| Pedicel texture | Sparsely prickly |
| Color pedicels | 144B yellow-green |
| Stamen number | 94.00 |
| Filament color | 196C greyed-green |
| Anther length (mm) | 0.62 |
| Anther width (mm) | 0.41 |
| Anther color—fresh | 157D green-white |
| Anther color—dry | 158C yellow-white |
| Pollen color | NN155D white |
| Amount of pollen produced | Abundant |
| Pistil number | 92.00 |
| Stigma color | 155C white |

TABLE 5-continued

| Characteristic | 'Kokanee' |
|---|---|
| Stigma shape | Frayed, ragged |
| Style length (mm) | 3.24 |
| Style color | 157C green-white |
| Ovary color | 144C yellow-green |
| Lateral measurements | |
| Peduncle length (mm) | 18.97 |
| Peduncle diameter (mm) | 1.33 |
| Peduncle texture | Sparsely prickly |
| Peduncle color | 144B yellow-green |

Table 6 shows primocane fruit characteristics of the new cultivar. Fruit characteristics include length, width, length/width ratio, receptacle length, receptacle diameter, drupelet length, drupelet width, number of drupelets per fruit, fruit weight, drupelet weight, individual seed weight, total seed weight per fruit, seed length, seed width, seed color, fruit glossiness, separation from receptacle, drupelet cohesion, firmness, flavor, fruit color, fruit color—immature, fruit color—maturing, fruit color—mature, titratable acidity, soluble solids, pH, anthocyanin content, harvest season, length of season, yield, and productivity.

TABLE 6

| Characteristic | 'Kokanee' |
|---|---|
| Length (mm) | 22.50 |
| Width (mm) | 19.33 |
| Length/width ratio (mm) | 1.16 |
| Receptacle length (mm) | 12.19 |
| Receptacle diameter (mm) | 5.85 |
| Drupelet length (mm) | 3.30 |
| Drupelet width (mm) | 3.20 |
| Number of drupelets per fruit | 132 |
| Weight (g) | 3.35 |
| Drupelet weight (mg) | 25.98 |
| Individual seed weight (mg) | 1.27 |
| Total seed weight per fruit (mg) | 165.65 |
| Seed length (mm) | 2.30 |
| Seed width (mm) | 1.33 |
| Seed color (dry) | 156A white |
| Glossiness | Medium |
| Separation from receptacle | Very easy |
| Drupelet cohesion | Coherent |
| Firmness | Firm |
| Flavor | Very good |
| Fruit color | Bright |
| Fruit color—immature | 164C greyed-orange |
| Fruit color—maturing | 47A red |
| Fruit color—mature | 53A red |
| Titratable acidity (% as citric acid) | 14.58 |
| Soluble solids (%; in Brix) | 12.44 |
| pH | 3.28 |
| Anthocyanin content (mg of cyanidin-3-glucoside/100 g) | 35.30 |
| Harvest season | 9 Aug-18 Sept |
| Length of season | Medium |
| Yield (actual kg · plant$^{-1}$) | 2.30 |
| Productivity | Medium-high |

We claim:

1. A new and distinct cultivar of red raspberry plant, substantially as illustrated and described, characterized by its moderate to high yields of large, bright-red-colored, firm, conic, sweet, flavorful fruit with excellent fresh fruit quality borne on primocanes in late summer.

* * * * *